United States Patent [19]
Baude et al.

[11] Patent Number: 5,172,143
[45] Date of Patent: Dec. 15, 1992

[54] ARTIFICIAL OPTICAL LENS AND METHOD OF MANUFACTURING IT

[75] Inventors: Dominique Baude, Saint Ouen; Jean-Claude Meslard, Saint Maurice; Gérard Obrecht, Issy Les Moulineaux; Pierre Chavel, Chilly-Mazarin; Denis Joyeux, Les Ulis; Jean Taboury, Sceaux, all of France

[73] Assignee: Essilor International Cie Generale d'Optique, Creteil, France

[21] Appl. No.: 641,710

[22] Filed: Jan. 15, 1991

[30] Foreign Application Priority Data

Jan. 22, 1990 [FR] France ............................. 90 00679
Nov. 16, 1990 [FR] France ............................. 90 14282

[51] Int. Cl.$^5$ .................... G02C 7/04; G02C 7/06; A61F 2/16
[52] U.S. Cl. .................... 351/177; 351/161; 351/169; 351/176; 623/6
[58] Field of Search ............ 351/159, 176, 177, 161, 351/169; 623/6

[56] References Cited

U.S. PATENT DOCUMENTS

| | | | |
|---|---|---|---|
| 3,610,924 | 10/1971 | Sinai | 250/49 |
| 3,993,485 | 11/1976 | Chandross et al. | 96/27 H |
| 4,541,969 | 9/1985 | Neefe | 264/1.4 |
| 4,707,236 | 11/1987 | Borowsky | 351/177 X |
| 4,943,150 | 7/1990 | Deichert et al. | 351/177 |

FOREIGN PATENT DOCUMENTS

| | | |
|---|---|---|
| 0145392 | 6/1985 | European Pat. Off. . |
| 207640 | 1/1987 | European Pat. Off. . |
| 2029178 | 10/1970 | France . |
| 2076194 | 10/1971 | France . |
| 618787 | 2/1949 | United Kingdom . |
| 636379 | 4/1950 | United Kingdom . |

OTHER PUBLICATIONS

Patents Abstracts of Japan, vol. 10, No. 216 (M-502)/2272/, Jul. 29, 1986; & JP-A-61 053 031, (Matsushita Electric Works, Ltd.), Mar. 15, 1986.
Patent Abstract of Japan, vol. 8, No. 180 (M-318)/1617/, Aug. 18, 1984; & JP-A-59 071 830, (Nihon Ita Glass K.K.), Apr. 23, 1984.

*Primary Examiner*—Scott J. Sugarman
*Attorney, Agent, or Firm*—Longacre & White

[57] ABSTRACT

The manufacture of an artificial optical lens having any given power profile starts from an artificial optical lens having a different power profile. A physical-chemical treatment method modifies the power profile to obtain a required power profile. A rotating mask is used for spatial modulation of the energy flux.

16 Claims, 4 Drawing Sheets

ARTIFICIAL OPTICAL LENS AND METHOD OF MANUFACTURING IT

BACKGROUND OF THE INVENTION

1. Field of the Invention

The present invention is generally concerned with artificial optical lenses, that is to say contact lenses or intra-ocular implants and ophthalmic lenses, that is to say eyeglass lenses, and it is more particularly directed to artificial lenses which have a radial profile of specific power to obtain a specific corrective action.

2. Description of the Prior Art

Contact lenses are currently manufactured by molding or by machining.

The advantage of molding is that the required power profile is obtained directly, by simple duplication of an appropriate mold.

However, only the external radius of curvature of the manufactured artificial contact lenses can then be varied, their inside radius of curvature having to remain within narrow and closely specified limits to achieve a good match to the radius of curvature of the cornea of the patient.

Manufacture by molding therefore requires that a large number of different molds be available.

These molds must cover all the ranges of powers required to correct all forms of ametropia.

In the case of contact lenses for correcting long sightedness, the molds must also cover all ranges of additional powers needed to correct all forms of long sightedness for each variety of ametropia to be corrected.

Manufacture by machining starts with a molded semi-finished product which is then mechanically processed to confer upon it the required power profile. This has the advantage of reducing the number of different molds required.

In practise, however, considerable processing has to be applied and is delicate and costly.

It has previously been proposed to apply physical-chemical processing to optical lenses.

This is the case, for example, with the published French patents Nos 2 029 178 and 2 076 194.

However, these French patents are essentially concerned with the manufacture of corrective lenses to be fitted to eyeglass frames. Although the first patent refers to the possibility of irradiating contact lenses, the irradiation is in practise by means of neutrons and its only purpose is to eliminate certain defects of the contact lenses.

These French patents are therefore not concerned with the manufacture of artificial optical lenses having a given power profile.

The Japanese patent document No JP-A-61 053031 proposes the use of physical-chemical processing to obtain a particular power profile, using a mask to achieve spatial modulation of the flux of energy to be controlled, but the initial substrate is merely a parallel sided slab.

The mask employed is also a static mask, which operates in terms of levels of grey, so to speak, and the blackening of which is in fact difficult to control.

A particular object of the present invention is a method for manufacturing an artificial optical lens with any given power profile that is advantageously free of these disadvantages.

SUMMARY OF THE INVENTION

In the method in accordance with the invention, starting from an artificial optical lens having some other power profile, physical-chemical processing is applied to modify the original power profile to achieve a required power profile, and a rotating mask is used for spatial modulation of the energy flux.

Thus like the method of manufacture by machining, the method in accordance with the invention starts with a semi-finished product which can therefore and advantageously be simpler, for example a simple spherical lens.

However, the method in accordance with the invention has the advantage that it is a physical-chemical method.

By locally modifying the refractive index of the material of the lens, or by locally modifying its thickness, or by modifying both the refractive index and the thickness, the physical-chemical processes currently available allow the power profile of a lens of this kind to be modified, in other words they allow modification of its optical characteristics such that it has the required power profile.

Many different physical-chemical processes can be used for this purpose.

These methods include, for example, photochemical methods, ion doping, photo-ablation and ion beam machining.

The use of a rotating mask for spatial modulation of the energy flux enables better control of this modulation.

It is found that the accuracy of a rotating mask is very much greater than that with which it is currently possible to control the blackening of a grey level static mask.

According to a further feature of the invention, the rotating mask further and advantageously lends itself to obtaining an astigmatic power profile, if required.

It is relatively simple to modulate the rotation speed of the rotating mask according to its angular position relative to the artificial optical lens being processed in order to obtain an astigmatic power profile for the lens.

In another aspect, the present invention consists in any artificial optical lens obtained by application of the method as defined hereinabove, that is to say any artificial optical lens having optical characteristics resulting from physical-chemical modification of initially different optical characteristics.

The objects, characteristics and advantages of the invention will emerge from the following description given by way of example and with reference to the appended diagrammatic drawings.

DETAILED DESCRIPTION OF THE INVENTION

Figure 1:
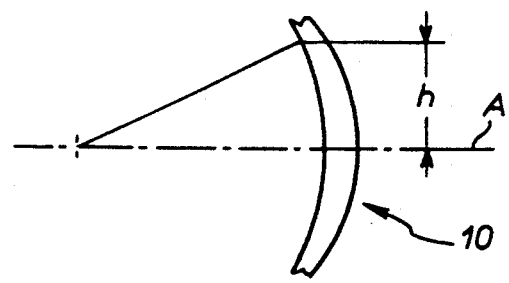
FIG. 1 is a partial view in axial cross-section of an artificial optical lens in accordance with the invention.

Referring to FIG. 1, the lens to be manufactured is a simultaneous vision contact lens 10 which, to correct long sightedness, has a power P(h) varying radially according to a specific aspherical profile.

This aspherical power P(h) may be expressed by the following polynomial:

$$P(h) = \sum_{i=0}^{i=7} a_i h^i \quad \text{(I)}$$

in which h is the distance in millimeters from the axis A of the contact lens 10 and $a_i$ represents a succession of numerical coefficients, of which in this instance there are eight.

The aspherical power P(h) may also be interpreted as the result of adding a basic spherical power $P_s$ and an "asphericalizing" power $P_a(h)$:

$$P(h) = P_s + P_a(h)$$

From the physical point of view, the contact lens 10 may be regarded as similar to a phase plate whose phase variation law or phase law (expressing the phase as a function of the distance h) is given by the equation:

$$\Phi(h) = 2\pi/l \times \int_0^h u \times P(u) \times du \quad \text{(II)}$$

in which 1 denotes the wavelength at which the light sensitivity of the eye is maximal.

For a spherical surfaces unifocal contact lens, this phase law represents the variation in the thickness of the lens relative to a parallel sided blade.

The manufacture of a contact lens 10 having the required aspherical power profile shown in FIG. 1 starts, in accordance with the invention, with a contact lens having some other power profile and processes this by a physical-chemical method to modify the original power profile to obtain that required.

The initial contact lens, which is not shown in the figures, is a spherical contact lens of power $P_o$, for example.

If the value $P_o = P_s$ is chosen, the asphericalizing power $P_a(h)$ to be added is written:

$$P_a(h) = P(h) - P_o \quad \text{(III)}$$

or, in terms of phase:

$$\Phi_a = 2\pi/l \times \int_0^h u \times P_a(u) \times du \quad \text{(III')}$$

In the most general case the physical-chemical processing employed results in modulation $D_n$ of the refractive index and modulation $D_e$ of the thickness.

Approximating to the first order, the corresponding phase modulation $D\Phi$ may be written in the form:

$$D\Phi = 2\pi/l[D_n \times e + (n - n_o)D_e] \quad \text{(IV)}$$

in which n is the refractive index of the material of the contact lens 10 and $n_o$ is that of the exterior medium.

It follows from what has been explained above that the expressions (III) and (IV) must be equivalent.

In other words, the following condition must apply:

$$D_n(h) \times e + (n - n_o) \times D_e(h) = \int_0^h u \times P_a(u) \times du$$

There are then two possibilities, depending on the nature of the physical-chemical treatment method.

In the first case the "dynamic range" of the method, by which is meant the maximal modulation of the pure refractive index and/or the maximal modulation of the pure thickness that can be achieved by applying this method, is sufficient to achieve the required phase excursion directly.

In the second case the dynamic range is not sufficient to achieve this variation in phase.

In this case, one possible solution is to modify the spherical power $P_o$ of the initial contact lens, in order to minimize the phase excursion required to achieve the necessary asphericalization.

To this end it suffices to add or subtract from the basic spherical power $P_s$ a dynamic power $P_d$.

If, in spite of this, the dynamic range of the physical-chemical treatment method employed is still insufficient to achieve the required phase excursion, a second solution in accordance with the invention is to reduce the phase law modulo $2\pi$.

As is well known, any phase value exceeding $2\pi$ can be reduced to an exactly equivalent value less than $2\pi$.

By reducing the phase law modulo $2\pi$ it is always possible to keep the required phase excursion below $2\pi$.

As mentioned above, many different physical-chemical treatment methods can be used to achieve the required asphericalization.

They include a photochemical method starting with a solid polymer material contact lens forming a matrix which is impregnated with a liquid that can be polymerized by light and incorporates a monomer and a photopolymerization initiator. The impregnated matrix is exposed to a source of radiation modulated according to the required asphericity, so as to polymerize the liquid impregnating it locally, according to this asphericity, after which the unpolymerized excess composition is removed.

To modulate the radiation to be applied to the matrix the corresponding energy flux is modulated spatially.

According to the invention this spatial modulation is obtained by the use of a rotating mask. Two numerical examples will now be given to provide a better illustration of the invention.

EXAMPLE 1

This example relates to a convergent contact lens 10 of total aspherical power P(h) having a basic spherical power $P_s$ and an additional asphericalization power $A_{dd}$ of 1.5 diopters.

By additional power $A_{dd}$ is meant here, in the conventional manner, the difference between the near vision power $P_{VP}$ and the distant vision power $P_{VL}$ (FIG. 2), it being understood that the corresponding near vision VP and far vision VL areas of the contact lens 10 have a particular geometrical size and that their power is the mean power for all of such an area.

As previously:

$$P(h) = P_s + P_a(h)$$

$$\text{and } P_a(h) = \sum_{i=0}^{i=7} a_i h^i$$

In this numerical example, the coefficients $a_i$ have the following values:
$a_0 = 1.8430572$
$a_1 = 0.030438234$
$a_2 = 0.92669499$
$a_3 = 0.52752879$
$a_4 = 1.1186199$
$a_5 = 0.79106624$
$a_6 = 0.30761219$
$a_7 = 0.04890526$ For convenience, a null value is chosen for $P_s$:

$$P(s) = 0$$

It will initially be assumed that the original contact lens also has a null spherical power.

It may be a parallel sided lens, for example.
Consequently:

$$P_o = 0$$

Figure 2:
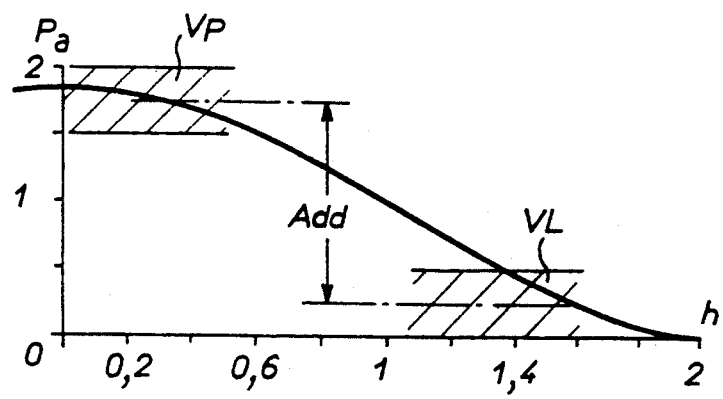
FIGS. 2 and 3 are two graphs relating to this lens, one showing the variation of the power of the lens as a function of the distance from the optical axis and the other showing the corresponding phase variation.

The graph in FIG. 2 plots the distance h in millimeters against the aspherical power $P_a$ in diopters to be applied to the active optical area of the original contact lens to obtain the required aspherical power profile for the contact lens 10.

The shaded areas in this diagram represent the near vision area VP and the far vision area VL of the contact lens 10.

In this example the near vision area VP is part of the central area of the contact lens 10 and the far vision area VL is part of its peripheral area.

However, it goes without saying that the opposite arrangement may be used.

Figure 3:
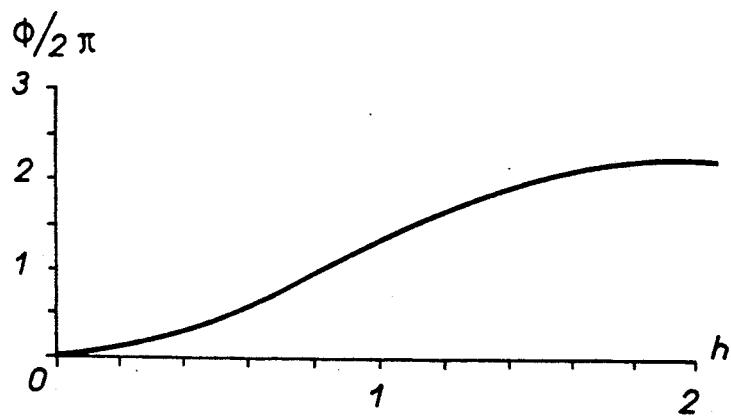

FIG. 3 shows the corresponding phase law.

For convenience, the phase $\Phi$ in this diagram is expressed as a multiple of $2\pi$.

The diagram shows that this multiple of $2\pi$ takes a value between 0 and 2.5.

The phase excursion to be covered is therefore in the order of $5\pi$.

If the physical-chemical treatment method used entails pure index modulation, the modulation required is $7 \times 10^{-3}$ for an original contact lens 200 μm thick.

If the physical-chemical treatment method used entails pure thickness modulation, the modulation required is 3.6 μm if the refractive index of the material of the original contact lens is 1.38.

The physical-chemical treatment method employed is, for example, a photochemical method of the kind briefly described above.

This photochemical method is described more fully in French patent application No 89 06323 filed May 12, 1989 and published under the number 2 646 930.

Figure 4:
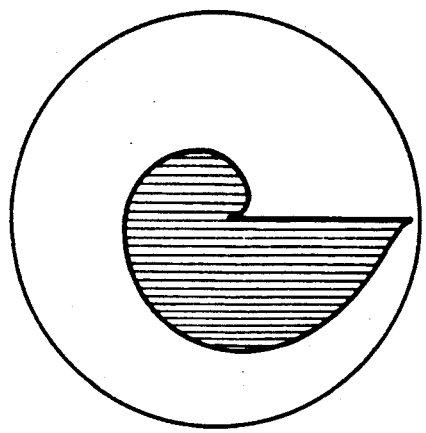
FIG. 4 is a plan view of a rotating mask used to manufacture the lens.

FIG. 4 shows a rotating mask for modulating spatially the corresponding flux of irradiation energy.

In FIG. 4 the opaque parts of the mask are shaded and the transparent parts are unshaded.

Assume that the original contact lens has a non-null spherical power $P_o$.

For example:

$$P_o = 0.6 \text{ diopter}$$

In this case:

$$P_o = P_s + P_d$$

with $$P_d = 0.6 \text{ diopter}$$

Figure 5:
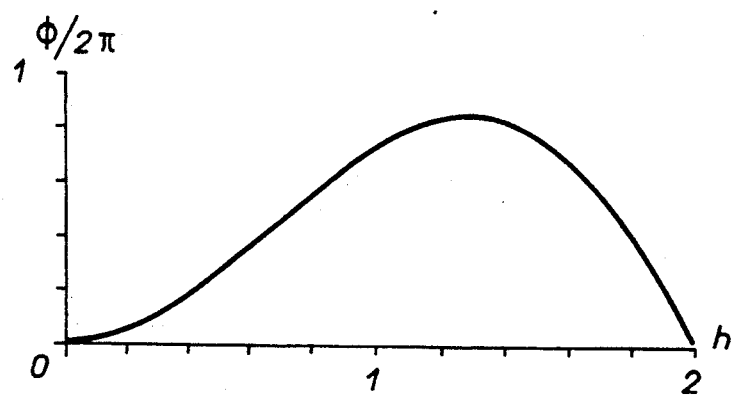
FIGS. 5 and 6 are respectively analogous to FIGS. 3 and 4 but relate to a different embodiment.
Figure 6:
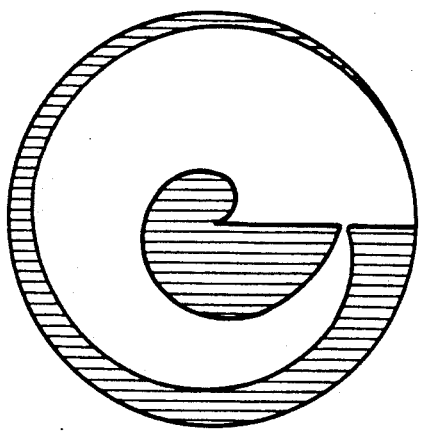

The phase law is as shown in the FIG. 5 diagram.
In the case of pure index modulation, the required modulation is $2.8 \times 10^{-3}$.
In the case of pure thickness modulation, the required modulation is 1.4 μm.
FIG. 6 shows the corresponding rotating mask.

EXAMPLE 2

The additional asphericalization power $A_{dd}$, given the same conditions as above, is 2.5 diopters.

Figure 7:
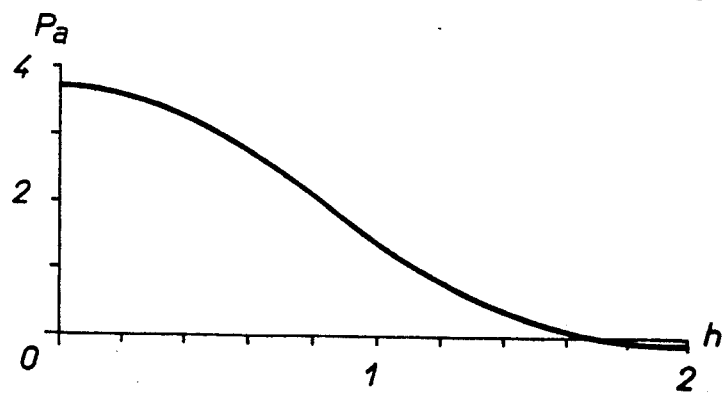
Figure 8:
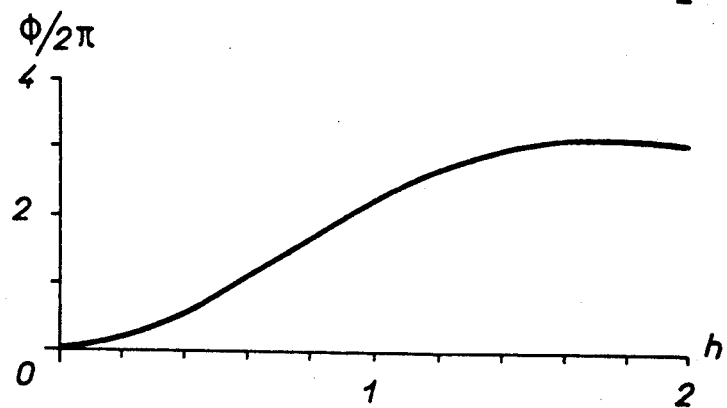

The values of the coefficients $a_i$ are therefore as follows:
$a_0 = 3.7110522$
$a_1 = 0.040382098$
$a_2 = 3.1321414$
$a_3 = 0.034659945$
$a_4 = 0.99060474$
$a_5 = 0.098949193$
$a_6 = 0.10272511$
$a_7 = 0.01788491$ If, as previously, $P_s$ and $P_o$ are equal to zero, the variation law for the asphericalization power $P_a$ is as shown in the FIG. 7 diagram and the phase law is as shown in the FIG. 8 diagram.

The phase excursion to be covered is in the order of $6\pi$.

In the case of pure index modulation the modulation required is $8.3 \times 10^{-3}$ for an original contact lens thickness of 200 μm.

In the case of pure thickness modulation the modulation required is 4.3 μm for an original contact lens material having a refractive index of 1.38.

Figure 9:
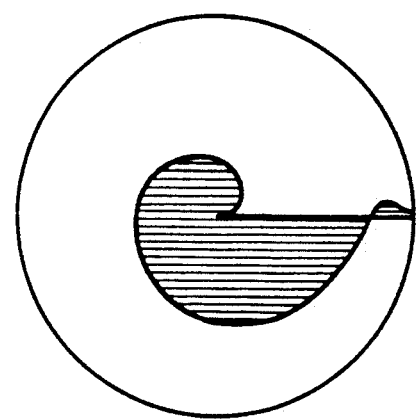
FIGS. 7, 8 and 9 are respectively analogous to FIGS. 2, 3 and 4 in the case of another artificial optical lens in accordance with the invention.

The rotating mask to be used is shown in FIG. 9.

Figure 10A:
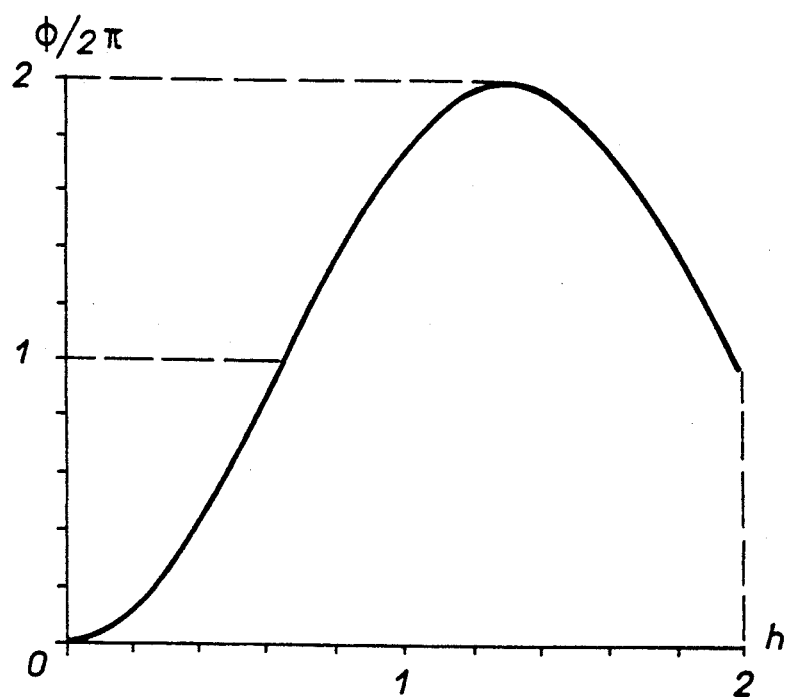
FIGS. 10A and 10B are graphs analogous to that of FIG. 5 and relating to this other artificial optical lens.

However, if the initial contact lens has a non-null positive power $P_o$, for example a positive power equal to 0.6 diopter, the phase law is as shown in the FIG. 10A diagram.

Figure 10B:
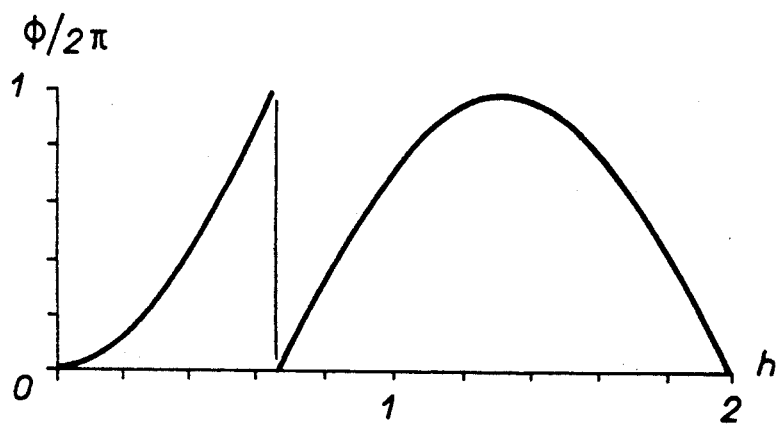

As the FIG. 10B diagram shows, it is possible to reduce the phase law modulo $2\pi$.

In the case of pure index modulation, the modulation required is $2.8 \times 10^{-3}$.

In the case of pure thickness modulation, the modulation required is 1.4 μm.

Figure 11:
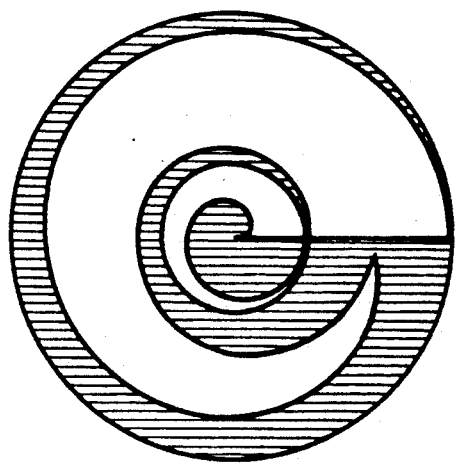
FIG. 11 is a view analogous to that of FIG. 6.
Figure 12:
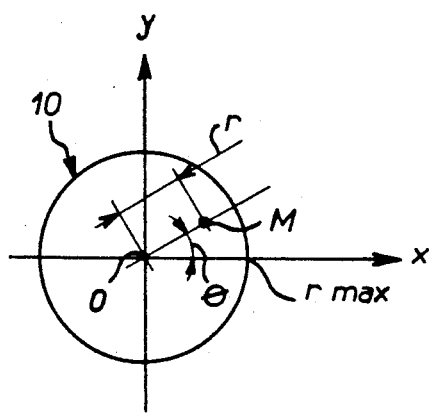
FIG. 12 is a plan view of the active optical area of an artificial optical lens to which a further feature of the invention can be applied.
Figure 13:
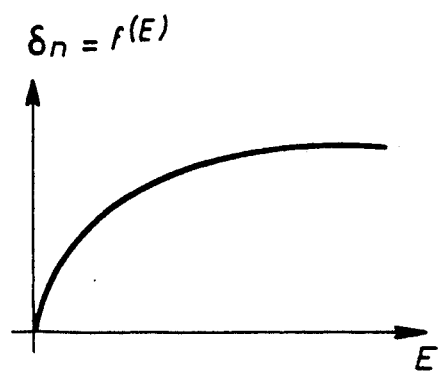
FIG. 13 is a diagram explaining this further feature.

FIG. 11 shows the corresponding rotating mask.

Of course, the numerical examples given must not be regarded as in any way limiting on the invention.

To the contrary, the invention encompasses all variants of execution and implementation. The invention is particularly applicable to the manufacture of unifocal contact lenses but also to the manufacture of spherical-toroidal contact lenses for correcting astigmatism.

Starting with a contact lens of constant power P, the method in accordance with the invention can produce a contact lens of greater constant power $(P+\Delta P)$.

Examples:

Let $\Delta P = 0.5$ D

The maximal phase for $h=2$ mm is $\Phi = 4\pi$

For pure thickness modulation: $D_e = 2.9$ μm

For pure index modulation: $D_n = 5.5 \times 10^{-3}$

Let $\Delta P = 0.25$ D

The maximal phase for $h=2$ mm is: $\Phi = 2\pi$

For pure thickness modulation: $D_e = 1.45$ μm

For pure index modulation: $D_n = 2.75 \times 10^{-3}$

The method in accordance with the invention can also produce artificial lenses for simultaneous correction of astigmatism and long sightedness. In this case, the initial lens is a spherical-toroidal artificial lens, in other words a lens of which one surface is spherical and the other is toroidal.

There will now be described with reference to FIGS. 12 through 15 a further feature of the invention whereby it is possible to obtain an astigmatic power profile, in other words artificial optical lenses whose power profiles on two mutually perpendicular axes are different.

A toroidal contact lens, that is to say a contact lens adapted to correct astigmatism, can be regarded as equivalent to a phase plate whose phase law in polar coordinates is of the form (compare equation (II) above):

$$\Phi(r, \theta) = \frac{2\pi}{\lambda} \times \frac{r^2}{2} (\cos^2\theta \times Px + \sin^2\theta \times Py) \qquad \text{(II')}$$

in which:

$\lambda$ is the wavelength at which the light sensitivity of the eye is maximal, Px and Py are the powers on the two mutually perpendicular axes Ox, Oy, and r is the distance from the origin O to any point M on the contact lens 10 concerned and $\theta$ is the angle between the corresponding radius and the Ox axis (FIG. 1).

For a contact lens, the active optical area must have at least a diameter of 6 mm.

Thus:

$r_{max} = 3$.

To simplify the explanation and provide a more concrete example, it is now assumed that the astigmatism required of the contact lens 10 is at most equal to 2 diopters.

Thus:

$\delta P max = |Px - Py| max = 2d$

Consequently:

$\delta\Phi max = 33\pi$

It will also be assumed that, as previously, the original contact lens is a spherical contact lens but in this instance the lens (not shown) is of constant thickness.

Finally, it will also be assumed that a photochemical treatment is applied to the original contact lens as explained above, in this instance a photopolymerization treatment, to obtain within it a localized variation of the refractive index adapted to modify its power profile (initially null) to obtain the required astigmatic power profile, using a rotating mask to achieve the required spatial modulation of the corresponding energy flux.

As the FIG. 2 diagram shows, the local variation of the refractive index $\delta n$ depends in practise on the energy E received during this photochemical treatment.

Thus:

$$\delta n = f(E) \qquad \text{(V)}$$

From the above equation (II'), this local variation $\delta n$ in the refractive index can also be written, in polar coordinates:

$$\delta n(r, \theta) = \frac{1}{K} \frac{r^2}{2} (\cos^2\theta \times \delta P + Py) \qquad \text{(II'')}$$

in which K is a constant.

Consequently:

$$E(r, \theta) = f^{-1}\left[\frac{r^2}{2K} (\cos^2\theta \times \delta P + Py)\right] \qquad \text{(VI)}$$

Figure 14:
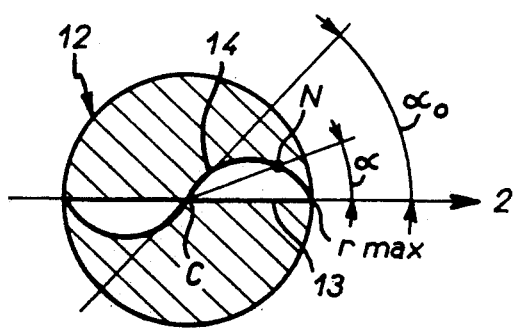
FIG. 14 is a plan view of the relevant rotating mask.

It will now be assumed that, as shown in FIG. 14, the transparent parts of the rotating mask 12 are each delimited by a straight line 13 used as the reference axis for the distance r and by a curve 14 passing through the center C and intersecting the previous curve 14 at the point $r_{max}$.

Let r and $\alpha(r)$ denote the polar coordinates of a point N on the curve 14 and $\alpha(o)$ be the angle of the tangent at this point through the origin C.

Figure 15:
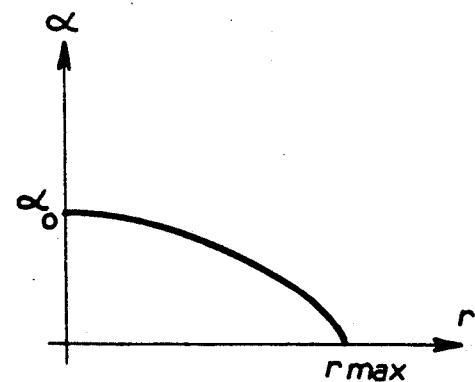
FIG. 15 is a diagram relating to one of the parameters conditioning the manufacture of this rotating mask.

The FIG. 15 diagram shows the curve for the angle $\alpha$ as a function of the distance r.

Finally, let $v(\theta)$ be the rotation speed of the rotating mask 12.

The energy that the rotating mask 12 allows to pass during the photochemical treatment applied to the basic contact lens can be written in the form:

$$E(r, \theta_o) = E_o \times \int_{\theta_0 - \frac{\alpha(r)}{2}}^{\theta_0 + \frac{\alpha(r)}{2}} \frac{d\theta}{v(\theta)} \qquad \text{(VII)}$$

If the rotation speed $v(\theta)$ is constant, and equal to $v_o$, for example, and if the law f is linear, a spherical contact lens of power $P_o$ is obtained.

The corresponding equations yield $E_o$ and $\theta_o$.

To obtain a toroidal contact lens, that is to say a contact lens having as astigmatic power profile, the rotation speed v is varied according to the angular position of the rotating mask 12 relative to the contact lens 10 being treated, this angular position being measured in terms of the angle $\theta$.

The above equations (VI) and (VII) then yield the new equation:

$$f^{-1}\left[\frac{r^2}{2K} (\cos^2\theta_o \times \delta P + Py)\right] = E_o \times \int_{\theta_o - \frac{\alpha(r)}{2}}^{\theta_o + \frac{\alpha(r)}{2}} \frac{d\theta}{v(\theta)} \qquad \text{(VIII)}$$

-continued that is:

$$r^2(\cos^2\theta_o \times \delta P + Px + Py) = K' \times \int_{\theta_o - \frac{\alpha(r)}{2}}^{\theta_o + \frac{\alpha(r)}{2}} \frac{d\theta}{v(\theta)}$$

in which K' is a constant.

The above equation (VIII) is an integral equation from which the required speed v(θ) can be determined.

Calculation shows that to a first approximation (neglecting the term in $\alpha^2$), the aberrations resulting from this approximation are in practise totally acceptable, this integral equation having a solution in the form:

$$\begin{cases} v(\theta) = \dfrac{v_o}{(Px + Py) + (Px - Py)} \cos^2\theta \\ \alpha(r) = a_o \times r^2 \end{cases}$$

in which, as briefly mentioned above, θ is the angle between the rotating mask 12 and the artificial optical lens being treated, in this instance the contact lens 10.

It is therefore a very simple matter to determine, for a given curve 14 delimiting the transparent parts of the rotating mask 12, in practise a conical section, the rotation speed v(θ) to be applied to the rotating mask 12 to obtain with appropriate approximation the required astigmatic profile for the contact lens 10 being treated.

Some numerical examples will now be given to provide a better illustration of the invention.

I. astigmatism: 2 d
   spherical power: −4 d
   a) basic lens: −1.75 d
      Px = −0.25 d
      Py = −2.25 d $$\alpha(r) = a_o \frac{r^2}{r\max^2} \quad a_o = 10°$$

$\delta n = 5 \times 10^{-2}$  $\delta\Phi\max = 37\pi$ b) basic lens: −4.25 d
   Px = +2.25 d
   Py = +0.25 d $$\alpha(r) = a_o \left(1 - \frac{r^2}{r\max^2}\right) \quad a_o = 10°$$

$\delta n = 5 \times 10^{-2}$  $\delta\Phi\max = 37\pi$

II. astigmatism: 1 d
    spherical power: −2 d
    a) basic lens: −0.75 d
       Px = −0.25 d
       Py = −1.25 d $$\alpha(r) = a_o \frac{r^2}{r\max^2} \quad a_o = 10°$$

$\delta n = 2 \times 8 \times 10^{-2}$  $\delta\Phi\max = 21\pi$ b) basic lens: −2.25 d
   Px = +1.25 d
   Py = +0.25 d $$\alpha(r) = a_o \left(1 - \frac{r^2}{r\max^2}\right) \quad a_o = 10°$$

-continued $\delta n = 2.8 \times 10^{-2}$  $\delta\Phi\max = 21\pi$

Of course, the present invention is not limited to these numerical examples but encompasses any variant implementation.

Its field of application is not limited to contact lenses alone, but to the contrary encompasses all artificial optical lenses and therefore ophthalmic lenses as well as ocular implants.

In all cases, the artificial optical lenses in accordance with the invention have optical characteristics, including astigmatic optical characteristics where appropriate, which are the result of physical-chemical modification of initially different optical characteristics.

Finally, although the examples given above are more particularly concerned with artificial optical lenses which are bodies of revolution, it goes without saying that the present invention applies equally to the manufacture of any other type of artificial optical lens.

We claim:

1. Method of manufacturing an artificial lens having a desired variable power profile comprising the steps of:
   (a) providing an artificial optical lens blank having an initial power profile;
   (b) providing a rotating mask having opaque and transparent zones mutually delimiting one another along a curved line of demarcation extending outwardly from a central zone toward a peripheral zone of the mask;
   (c) subjecting the artificial optical lens blank to a physical-chemical treatment employing an energy flux for modifying the initial power profile to the desired variable power profile;
   (d) rotating the mask relative to the artificial lens blank during the physical-chemical treatment of step (c) for effecting spatial modulation of the energy flux.

2. Method according to claim 1 wherein the initial artificial optical lens blank is a spherical lens blank.

3. Method according to claim 2 wherein the initial artificial optical lens blank is a spherical-toroidal lens blank.

4. Method according to claim 1 wherein the modification of the power profile is in accordance with a phase law, the phase law being reduced to maintain the phase excursion below $2\pi$.

5. Method according to claim 4 wherein the energy flux is modulated in accordance with a phase law, the phase law being reduced a modulo $2\pi$.

6. Method according to claim 1 wherein the modulation of the physical-chemical treatment consists of modulating a characteristic, wherein the characteristic is selected from the group consisting of refractive index and lens thickness.

7. Method according to claim 1 wherein the physical-chemical treatment is a photochemical method.

8. Method according to claim 1 wherein the desired power profile is astigmatic, and comprising varying the rotational speed of the mask in accordance with the angular position of the artificial optical lens blank relative to the mask.

9. Method according to claim 8 wherein the rotational speed (v) is varied according to the following equation:

$$v(\theta) = \frac{v_0}{(P_x + P_y) + (P_x - P_y)\cos 2\theta}$$

in which $\theta$ is the angular position between the rotating mask and the artificial optical lens blank, and Px and Py are the powers to be obtained along two mutually perpendicular axes.

10. Method according to claim 1 wherein the mask rotates about a center of rotation, and the transparent and the opaque zones are further delimited by a straight line intersecting the curved line which passes through the center of rotation of the mask.

11. Method according to claim 10 wherein the curved line is a conical section.

12. Method of manufacturing an artificial lens having a desired astigmatic power profile comprising the steps of:
   (a) providing an artificial optical lens blank having an initial power profile;
   (b) providing a rotating mask having opaque and transparent zones mutually delimiting one another along a curved line of demarcation extending outwardly from a central zone toward a peripheral zone of the mask;
   (c) subjecting the artificial optical lens blank to a physical-chemical treatment, the treatment including modulating a characteristic, wherein the characteristic is selected from the group consisting of refractive index and lens thickness;
   (d) employing an energy flux for modifying the initial power profile to the desired variable power profile including;
   (e) rotating the mask relative to the artificial lens blank during the physical-chemical treatment of step (c) for effecting spatial modulation of the energy flux; and
   (f) varying the rotational speed of the mask in accordance with the angular position of the artificial optical lens blank relative to the mask.

13. Method of manufacturing an artificial lens having a desired power profile comprising the steps of:
   (a) providing an artificial optical lens blank having an initial power profile;
   (b) providing a mask having opaque and transparent zone;
   (c) subjecting the initial artificial optical lens to a physical-chemical treatment employing an energy flux for modifying the initial power profile to the desired power profile;
   (d) rotating the mask relative to the artificial lens blank during the physical-chemical treatment of step (c) for effecting spatial modulation of the energy flux; and
   (e) modifying the power profile in accordance with a phase law, the phase law being reduced to maintain the phase excursion below $2\pi$.

14. Method of manufacturing an artificial lens having a desired variable power profile comprising the steps of:
   (a) providing an artificial optical lens blank having an initial power profile;
   (b) providing a mask having opaque and transparent zone;
   (c) subjecting the artificial optical lens blank to a physical-chemical treatment employing an energy flux for modifying the initial power profile to the desired variable power profile; and
   (d) rotating the mask relative to the artificial lens blank during the physical-chemical treatment of step (c) for effecting spatial modulation of the energy flux, modulation of the physical-chemical treatment consisting of modulating a characteristic, wherein the characteristic is selected from the group consisting of refractive index and lens thickness.

15. Method of manufacturing an artificial lens having a desired astigmatic power profile comprising the steps of:
   (a) providing an artificial optical lens blank having an initial power profile;
   (b) providing a rotating mask having opaque and transparent zone;
   (c) subjecting the artificial optical lens blank to a physical-chemical treatment employing an energy flux for modifying the initial power profile to the desired variable power profile;
   (d) rotating the mask relative to the artificial lens blank during the physical-chemical treatment of step (c) for effecting spatial modulation of the energy flux; and
   (e) varying the rotational speed of the mask in accordance with the angular position of the artificial optical lens blank relative to the mask.

16. Artificial optical lens manufactured according to a method in which there is provided an artificial optical lens blank having an initial power profile, a mask rotatable relative to the optical lens blank having opaque and transparent zones mutually delimiting one another along a curved line of demarcation extending outwardly from central zone towards a peripheral zone of the mask, and the artificial optical lens blank is subjected to a physical-chemical treatment employing an energy flux for modifying the initial power profile to the desired variable power profile, and the mask is rotated relative to the artificial lens blank during the physical-chemical treatment for effecting spatial modulation of energy flux.

* * * * *